(12) United States Patent
Fetzer

(10) Patent No.: US 6,527,398 B1
(45) Date of Patent: Mar. 4, 2003

(54) TUBULAR-WAVEGUIDE GAS SAMPLE CHAMBER FOR OPTICAL SPECTROMETER, AND RELATED METHODS

(76) Inventor: Gregory J. Fetzer, 11251 E. Placita Rancho Grande, Tucson, AZ (US) 85730

(*) Notice: Subject to any disclaimer, the term of this patent is extended or adjusted under 35 U.S.C. 154(b) by 0 days.

(21) Appl. No.: 09/590,321

(22) Filed: Jun. 8, 2000

(51) Int. Cl.[7] .................. G01N 21/61; G01N 21/05
(52) U.S. Cl. ........................ 354/437; 356/440
(58) Field of Search ....................... 356/246, 437, 356/440; 250/343

(56) References Cited

U.S. PATENT DOCUMENTS

| | | | | |
|---|---|---|---|---|
| 3,997,786 A | * | 12/1976 | Lauer et al. | 250/343 |
| 4,190,363 A | * | 2/1980 | Adrian | 356/440 |
| 4,228,352 A | * | 10/1980 | Adrian | 250/343 |
| 5,103,096 A | * | 4/1992 | Wong | 250/343 |
| 5,696,379 A | * | 12/1997 | Stock | 250/343 |

* cited by examiner

Primary Examiner—Richard A. Rosenberger
(74) Attorney, Agent, or Firm—Ashen & Lippman

(57) ABSTRACT

Apparatus and method are introduced for detecting and measuring a gas within a gaseous specimen by radiation-absorption spectroscopy. The apparatus includes a housing, and a coiled waveguide arranged in the housing—with a radiation inlet for receiving radiation and a radiation outlet for emitting the received radiation. The housing has a gas entry chamber enclosing a first portion of the waveguide to receive the gas; and a gas exhaust chamber on the opposed side of the waveguide enclosing a second portion of the waveguide and adapted to exhaust the gaseous specimen. Perforated openings are formed in the first and second portions—providing short paths for flow of the specimen from the entry chamber through the guide into the exhaust chamber. A laser projects electromagnetic radiation into the inlet of the guide, and a photodetector receives the radiation from the outlet. A signal processor for analyzing the output of the detector identifies and determines the concentration of at least one gas within the gas specimen. Laser drilling and other techniques are prescribed for perforating the waveguide.

57 Claims, 6 Drawing Sheets

TUBULAR-WAVEGUIDE GAS SAMPLE CHAMBER FOR OPTICAL SPECTROMETER, AND RELATED METHODS

BACKGROUND

1. Field of the Invention

This invention relates generally to absorption spectroscopy; and more particularly to a waveguide and apparatus for the detection and measurement of trace gases, preferably absorption spectroscopy—and most preferably by wavelength-modulation absorption spectroscopy.

2. Related Art

Much of the development of today's pollution monitoring equipment was carried out after passage of the Clean Air Act. At that time electrooptical technology was in its infancy in comparison with current capabilities. One of the primary disadvantages of optical techniques for gas detection and measurement is that instruments tend to be large and complex.

Analyzers that meet the EPA designated reference method require specialized techniques for specific gases. For example, $NO_2$ is detected by chemiluminescence; CO by gas correlation; $O_3$ by absorption; and $SO_2$ by fluorescence. There has been no single effective methodology that could be used to monitor key pollutants of interest.

Current analyzers are typically packaged one to a 48 cm (19 inch) rack-mounted chassis. These analyzers typically weigh nearly 25 kg, including the required sample handling components, power supplies and electronics. Ambient air monitoring stations tend to involve buildings to enclose the analyzers and other sophisticated support equipment, and dramatically increase the cost associated with pollution assessment.

Similar problems exist for continuous emission monitoring systems used to evaluate flue gas from coal- and gas-fired electrical generation facilities. In many cases analyzers are mounted inside large dedicated shelters. Samples of the flue gas are transported over long distances in heated sample lines from the stack to the shelters.

Ultraviolet absorption bands of gases tend to be relatively broad due to the nature of the changes experienced by the molecules. There are significant overlaps in spectral features of different molecules.

Spectral selectivity is required to overcome the inherent problem of interference. Lamp inefficiencies also require high heat dissipation. Several UV instruments have been used for pollution monitoring; however, these systems are relatively large and require complicated spectral deconvolution algorithms to eliminate interference.

Both infrared and ultraviolet techniques require relatively long light/sample interaction paths to achieve sensitive detection capabilities. This has been achieved using multipass cells that reflect the light repeatedly over a folded path inside a container that holds the sample.

To achieve adequate pathlengths these cells are often large (>1000 cc) in volume. Noise and drift associated with the measurements impose strict design criteria to maintain alignment of the cells. Cell temperatures are usually controlled to maintain stability, and large pumps are required to achieve rapid pneumatic response.

A prior-art device that potentially provides a more compact gas analyzer is shown in U.S. Pat. No. 5,341,214 to Wong. This patent discloses an inherently rigid cylindrical waveguide/chamber having an internal blackbody radiation source mounted within one end, and two infrared detectors mounted within the opposite end of the chamber.

The radiation is reflected at the walls of the chamber to increase the light path. Each detector includes an optical filter; one filter defines a spectral band that coincides with the infrared absorption of the gas to be measured, and the other defines a nonabsorption bandpass.

The signals from Wong's detectors are processed to provide a ratio related to the concentration of the gas in the sample. The chamber includes a membrane-covered inlet aperture and an outlet aperture to permit flow through the chamber.

A device utilizing this technology is likely suited to detect only a high concentration of a gas. Short optical pathlength limits sensitivity for low concentrations, and the low gas flow limits the response time.

Another prior-art device is shown in U.S. Pat. No. 5,384,640, also to Wong. This patent discloses an evidently rigid cylindrical waveguide/chamber having an integral laser positioned within one end of the chamber, and an integral detector positioned within the opposite end.

Apertures in the wall of the chamber enable flow of gas through the chamber. The cylinder can be partitioned into successive chambers for the detection of different gases. The chamber is relatively large, having a diameter greater than the diameters of the laser and the detector, and therefore as a practical matter is quite limited in optical length and also optical efficiency. From the smallest commercially available laser and detector packaging, it can be seen that the inside diameter of Wong's chamber is at least 5 mm.

Consequently a device based on this patent too appears limited to measuring only high concentrations of a gas, and only by direct absorption (not by wavelength-modulation absorption). The optical length and resulting sensitivity are further limited by partitioning the chamber for the detection of multiple gases.

U.S. Pat. No. 5,696,379 to Stock discloses a prior-art infrared absorption device incorporating a curved tubular waveguide having a plurality of random gas inlets along the length of the waveguide and having an internal radiation source within the waveguide. A second radiation source is positioned within the waveguide near detectors and utilized to compensate for deterioration drift and temperature drift of the detectors. A device based upon this patent is believed to have a relatively large-diameter, low-efficiency waveguide with a relatively short optical path, and consequently to have limited sensitivity and slow response times between measurements.

There have been significant recent developments in hollow optical waveguides for energy delivery in the infrared regions (0.8 to 12 p) of the spectrum. Such improvements are disclosed in U. S. Pat. No. 5,440,664; 5,567,471; and 5,815,627 to Harrington et al., and are assigned to Rutgers, The State University of New Jersey. This technology provides waveguides for preservation of good transverse coherence of input infrared laser radiation, and that transmit substantial power of such radiation with low attenuation. The waveguide typically comprises a small-diameter, thin-wall silica glass tube, a protective outer coating, a reflective layer on the inner surface of the tube, and a dielectric coating on the exposed surface of the reflective layer.

Heretofore, this new waveguide technology has not been effectively applied and packaged for compact absorption spectroscopy.

There have also been significant recent developments of semiconductor diode lasers and the quantum cascade laser.

Such improvements represent new compact tunable near- and midinfrared coherent light sources that can operate at room or thermoelectric control temperatures, and can be customized for specific wavelengths.

The explosive growth and miniaturization of electronics provides high-speed analog-to-digital converters and high-throughput digital signal processing capabilities, that have heretofore not been applied and incorporated into systems for compact, accurate and reliable absorption spectroscopy.

As shown above, the related art remains subject to significant problems and has left room for considerable refinement.

SUMMARY OF THE DISCLOSURE

The present invention introduces such refinement, and provides a novel waveguide and optical gas-sensor apparatus that is compact, lightweight, durable, extremely sensitive, accurate and reliable, and has a rapid response time.

The invention has several independently usable facets or aspects, which will now be introduced. In preferred embodiments of a first of its main aspects or facets, the present invention is a waveguide for holding a gaseous specimen for spectral analysis.

The waveguide includes a hollow elongated tube having an interior with inside diameter not exceeding two millimeters (2 mm), a radiation inlet and a radiation outlet—and also having a wall with a substantially smooth reflective inner surface, adapted for guiding radiation along the interior. In addition the waveguide includes some means for passage of the gaseous specimen through the wall into the interior of the tube. For purposes of breadth and generality in discussing the invention, these means may be called simply the "passage means".

The foregoing may be a description or definition of the first facet or aspect of the present invention in its broadest or most general form. Even as couched in these broad terms, however, it can be seen that this facet of the invention importantly advances the art and resolves certain of the previously outlined problems.

In particular, because of its small diameter the waveguide can be curved or bent and thereby made extremely compact in any number of very favorable configurations—a very long tube being configurable, in particular, into a very small volume. Useful arrangements include disorderly or chaotic stacks, as well as geometrical forms that are regular.

In contrast with the previously discussed larger-diameter, inherently rigid Wong devices, for instance, this first aspect of the invention can provide an extremely long optical path for very high sensitivity. No correspondingly bulky or heavy enclosure, frame, etc. is required.

Furthermore the small diameter imparts to the waveguide a degree of resilience, even after its fabrication into a module of an apparatus, and thereby an immunity to common kinds of damage that derive inherently from rigid and accordingly brittle constructions. Hence the waveguide of the first aspect of the invention is immediately conducive to important advances in provision of a fully portable, small, lightweight and also very robust gas spectrometer.

Although the first major aspect of the invention thus significantly advances the art, nevertheless to optimize enjoyment of its benefits preferably the invention is practiced in conjunction with certain additional features or characteristics. In particular, preferably the passage means include a first portion of the tube, having at least one perforated opening through its wall, adapted for receiving the gaseous specimen. The passage means preferably also include a second portion of the tube, also having at least one perforated opening through its wall, adapted for exhausting the gaseous specimen.

In this case it is furthermore preferable that the tube be shaped into a coil having at least one loop, and that the first portion and the second portion be on opposed sides of the coil. In this way the tube is adapted to provide two or more paths by which the gaseous specimen can flow, in the tube. As will be made more clear shortly, the tube thus provides two or more gas-flow paths even if the coil has only one loop.

Also in this case preferably the waveguide includes a housing supporting the tube, and having a gas entry chamber and a gas outlet chamber. The inlet chamber encloses the first portion of the tube and is adapted for receiving the gaseous specimen, and the exhaust chamber encloses the second portion of the tube and is adapted for exhausting the gaseous specimen.

Additional preferences related to the preferred coiled configuration of the waveguide include these:

the tube has an inner diameter in arrange of about 250 to 2000 $\mu$m and a length in a range of about three to twenty meters;

the coil has a radius of curvature in the range of about five to twenty centimeters and a number of loops in a range of about eight to sixty-five;

in the first portion, each of the loops has at least one perforated opening therein, of diameter in a range of about ten to one hundred micrometers; and in the second portion, each of the loops has at least one perforated opening therein, of diameter in the range of about ten to one hundred micrometers.

Still further preferences related to the coiled form of the invention include, for the tube, inner diameter of about one-half millimeter and length of about tan meters; and for the coil, a radius of about five centimeters and loop count of about thirty-one and a half. In both the first and second portions, preferably each loop has plural perforated openings of diameter about fifty micrometers.

In preferred embodiments of a second major independent facet or aspect, the invention is apparatus for detecting and determining a concentration of at least one gas within a gaseous specimen by radiation-absorption spectroscopy. The apparatus includes a coiled hollow waveguide having a radiation inlet and a radiation outlet, and the waveguide is adapted for guiding radiation along its interior.

The apparatus also includes some means for providing a plurality of paths for flow of the gaseous specimen within the waveguide. Again for purposes of breadth and generality these means will be called the "providing means".

Also included are some means for projecting radiation along the interior of the waveguide to irradiate the gaseous specimen. These means, again for generality and breadth, will be called the "projecting means".

The apparatus still further includes some means for analyzing the radiation emerging from the gaseous specimen to detect and determine the concentration of at least one gas in the specimen. These means, as before, will be called the "analyzing means".

The foregoing may represent a description or definition of the second aspect or facet of the invention in its broadest or most general form. Even as couched in these broad terms, however, it can be seen that this facet of the invention importantly advances the art.

In particular, while this aspect of the invention is capable of providing plural gas-flow paths across the coiled waveguide, the optical-absorption path can most naturally extend along the entire waveguide for a single continuous distance. Therefore the invention enjoys an extremely favorable relationship between rapidity of gas changeover (for very quick response to changes in gas constituents) and a long optical path for extremely high optical-absorption sensitivity.

Although the second major aspect of the invention thus significantly advances the art, nevertheless to optimize enjoyment of its benefits preferably the invention is practiced in conjunction with certain additional features or characteristics. In particular, preferably the means for providing a plurality of paths include the coiled waveguide having at least one complete loop.

In this preferred configuration, a first portion of each loop and a second portion of each loop are at opposed sides of the coiled waveguide. The first portion has at least one perforated opening for receiving the specimen, and the second portion has at least one perforated opening for exhausting the specimen.

Accordingly the plurality of paths includes two half-loop paths across each loop, respectively. The second portion, in this preferred form of the invention, has an exhaust pump for exhausting the specimen, which impels flow of the specimen through the waveguide.

Another preference is that the projecting means include a laser disposed to project radiation into the inlet of the waveguide. Here the laser preferably includes a semiconductor laser—and most preferably a semiconductor quantum cascade laser.

Yet another preference is that the analyzing means include a photodiode disposed to receive the radiation emitted from the outlet of the waveguide, and signal processing means for analyzing the output of the photodiode. Still another basic preference is that the apparatus include some means for displaying the output of the analyzing means, and also some means for control of operation of the apparatus by an operator—here called the "displaying means" and "control means" respectively. In this latter case the displaying means and the control means are adapted for operation at a location remote from the source of the gaseous specimen.

In preferred embodiments of a third major independent facet or aspect, the invention is apparatus for detecting and determining a concentration of two or more respective specific gases within a gaseous mixture specimen. The apparatus includes a coiled hollow waveguide having a radiation inlet and a radiation outlet, and is adapted for guiding radiation along the interior.

Also included are some means for providing a plurality of paths for flow of the gaseous specimen within the waveguide. For reasons outlined earlier these means will be called the "providing means".

The apparatus additionally includes some means for sensing and recording spectra for the plural specific gases of the gaseous specimen. These will be called the "sensing and recording means".

Yet further included are some means for projecting radiation along the interior of the waveguide, to be absorbed by each of the plural specific gases therein; and also some means for analyzing the radiation emerging from the gaseous specimen. These means will be called the "projecting means" and the "analyzing means", respectively.

The foregoing may represent a description or definition of the third aspect or facet of the invention in its broadest or most general form. Even as couched in these broad terms, however, it can be seen that this facet of the invention importantly advances the art.

In particular, this aspect of the invention provides the capability, in a very economical instrument, for determining the presence and quantities of two or more gases—and also, perhaps more interestingly, for characterizing relatively complicated conditions. That is, the invention is not limited to quantifying levels of two or more gases as such.

It also can be configured to gauge favorable or unfavorable conditions for a mechanism (e. g. emissions control in a motor vehicle), or for a factory (e. g. quality control in a petroleum-cracking process stream). It can serve in any one of a very great variety of confined workspaces ranging from sewer lines to mines to submarines (e. g. monitoring for explosive or other hazardous atmospheres).

Although the third major aspect of the invention thus significantly advances the art, nevertheless to optimize enjoyment of its benefits preferably the invention is practiced in conjunction with certain additional features or characteristics. In particular, preferably the projecting means include a tunable laser for projecting radiation into the waveguide inlet—more preferably a semiconductor laser, and ideally a semiconductor quantum cascade laser.

A variety of selectable preferences for the plural-gas analyzing forms of the invention will now be mentioned. It will become clear that these preferences respectively correspond to different industrial or other applications, such as suggested above.

In one such preference the plural respective gases include at least one of $NH_3$, $CO_2$ and $H_2O$; and here the laser is tunable within the near-infrared spectrum at about 1.54 $\mu$m. In other preferences the plural gases within the gaseous mixture specimen include at least one of these gases:

in one case, $NH_3$, $CO_2$, $CH_4$, $H_2O$, and NO;

in another case, NO, $NO_2$, $SO_2$, $NH_3$, CO, $CO_2$, and $H_2O$;

in yet another case, HF, $O_2$, $H_2O$, and $O_3$; and in still another case, NO, $NO_2$, $CH_4$, BTX and VOCs.

In preferred embodiments of a fourth major independent facet or aspect, the invention is a handheld self-contained portable apparatus for detecting and measuring at least one gas within a gaseous specimen by radiation-absorption spectroscopy. The apparatus is for use with a portable source of energy for powering the apparatus.

It includes a coiled waveguide having a radiation inlet and a radiation outlet—and adapted for guiding radiation along its interior. It also includes some means for providing flow of the specimen within the interior of the waveguide—the "flow providing means"—and some means for projecting radiation along the interior of the waveguide to irradiate the gaseous specimen, the "projecting means".

Also included are some means for analyzing the radiation emerging from the gaseous specimen—the "analyzing means"—to detect and determine the concentration of at least one gas in the specimen. Also included in the apparatus are some means—the "housing means"—for enclosing the waveguide, the projecting means, the analyzing means, the path-providing means and the flow-providing means.

The foregoing may represent a description or definition of the fourth aspect or facet of the invention in its broadest or most general form. Even as couched in these broad terms, however, it can be seen that this facet of the invention importantly advances the art.

In particular, this form of the invention provides portability and compactness in a full-capability gas analyzer. These features promise to be extremely valuable for sensitive measurements under difficult field conditions —whether in remote, rugged areas or for mobile operation in large cities, or in other kinds of challenging environments such as outlined earlier.

Although the fourth major aspect of the invention thus significantly advances the art, nevertheless to optimize enjoyment of its benefits preferably the invention is practiced in conjunction with certain additional features or characteristics. In particular, preferably the apparatus has overall dimensions not exceeding about twenty-five centimeters by thirty centimeters by eight centimeters (25 by 30 by 8 cm).

Preferably its weight is about three kilograms (3 kg) at most. Preferably the projecting means include a laser adapted to project radiation into the inlet of the waveguide; and the analyzing means include a photodiode adapted to receive the radiation emitted from the outlet of the waveguide, as well as signal processing means adapted for analyzing the output of the photodiode.

Another preference is that the housing means include a housing supporting the waveguide in coiled loops. Here the housing has an inlet chamber enclosing a first portion of the loops and receiving the gaseous specimen therein, and has an exhaust chamber enclosing a second portion of the loops and exhausting the gaseous specimen therefrom. In this case the invention also includes some means for controlling the apparatus, and some means for displaying its resulting analysis.

In preferred embodiments of a fifth major independent facet or aspect, the invention is a method for adapting an elongated hollow waveguide for flow of a gaseous specimen through the wall of the waveguide. The method includes the step of providing an elongated hollow waveguide that is flexible.

It also includes the step of forming at least one perforated opening through a first portion of the wall of the flexible waveguide for entry of the gaseous specimen. Another included step is forming at least one perforated opening through a second portion of the wall of the flexible waveguide for exhaust of the gaseous specimen.

The foregoing may represent a description or definition of the fifth aspect or facet of the invention in its broadest or most general form. Even as couched in these broad terms, however, it can be seen that this facet of the invention importantly advances the art.

In particular, this novel method is key to very efficiently preparing a module that can serve as both a high-quality waveguide and a flow cell. Although the fifth major aspect of the invention thus significantly advances the art, nevertheless to optimize enjoyment of its benefits preferably the invention is practiced in conjunction with certain additional features or characteristics. In particular, the several apparatus aspects and preferences introduced above are applicable in regard to this method form of the invention as well.

In preferred embodiments of a sixth major independent facet or aspect, the invention is a method for adapting an elongated hollow waveguide, for a plurality of paths of flow of a gaseous specimen through the wall of the waveguide. The method includes the step of securing the waveguide into a coil having at least one loop.

A gas entry portion of each loop and a gas exhaust portion of each loop are at opposed sides of the coil. The method also includes the step of forming at least one perforated opening through the wall of substantially each loop in the entry portion, for entry of the gaseous specimen.

Another step is forming at least one perforated opening through the wall of substantially each loop in the exhaust portion, for exhaust of the gaseous specimen. In this way, substantially each of the perforated loops provides two—or roughly two—half-loop paths for flow of the gaseous mixture from the entry portion to the exhaust portion.

The foregoing may represent a description or definition of the sixth aspect or facet of the invention in its broadest or most general form. Even as couched in these broad terms, however, it can be seen that this facet of the invention importantly advances the art.

In particular, this aspect of the invention serves very well for efficiently preparing a module that can serve as both a high-quality waveguide and high-throughput flow cell. Although the sixth major aspect of the invention thus significantly advances the art, nevertheless to optimize enjoyment of its benefits preferably the invention is practiced in conjunction with certain additional features or characteristics.

In particular, there are several selectable preferences as to the two forming steps. These preferences include employing the step of laser drilling, or chemical etching, or photolithography, or electrostatic discharge.

Another preference is that the forming steps include forming the perforated openings having a diameter about one-tenth the inner diameter of the waveguide. A preferred result of the method is a waveguide produced by the specified method. That waveguide preferably has an inside diameter of about one-half millimeter and perforated openings of diameter about fifty micrometers.

In preferred embodiments of a seventh major independent facet or aspect, the invention is apparatus for detecting and measuring at least one gas within a gaseous specimen by radiation-absorption spectroscopy. The apparatus includes a housing.

It also includes an elongated coiled hollow flexible waveguide arranged within the housing. The waveguide has a radiation inlet adapted for receiving radiation, and in addition a radiation outlet adapted for emitting the received radiation.

The housing has a gas entry chamber enclosing a first portion of the waveguide and adapted for receiving the gaseous specimen. It also has a gas exhaust chamber enclosing a second portion of the waveguide and adapted for exhausting the gaseous specimen. The first portion and the second portion are on opposed sides of the coiled waveguide.

The first portion includes part of at least one loop of the waveguide. At least one perforated opening is defined in that part of the waveguide, so that the interior of the waveguide is in communication with the gas entry chamber.

The second portion includes part of at least one loop of the waveguide. At least one perforated opening is defined in that part of the waveguide too, so that the interior of the waveguide is in communication with the exhaust chamber. The gaseous specimen flows from the inlet chamber through the waveguide into the exhaust chamber.

An exhaust pump is connected to the exhaust chamber for providing flow of the specimen through the waveguide. A source is adapted for projection of electromagnetic radiation into the inlet of the waveguide, and a detector is adapted for receiving the radiation emitted from the outlet of the waveguide. The apparatus also includes a signal processor for analyzing the output of the detector to identify and determine the concentration of at least one gas within the gas specimen.

The foregoing may represent a description or definition of the seventh aspect or facet of the invention in its broadest or most general form. Even as couched in these broad terms, however, it can be seen that this facet of the invention importantly advances the art.

In particular, this apparatus combines most of the beneficial features of the previously introduced aspects of the invention. It accordingly represents a very powerful and sophisticated tool for gas analysis with a compact, lightweight, robust, and high-gas-throughput sensor.

Although the seventh major aspect of the invention thus significantly advances the art, nevertheless to optimize enjoyment of its benefits preferably the invention is practiced in conjunction with certain additional features or characteristics. In particular, the several preferences described in earlier passages of this section are applicable here as well.

All of the foregoing operational principles and advantages of the present invention will be more fully appreciated upon consideration of the following detailed description, with reference to the appended drawings, of which:

DETAILED DESCRIPTION OF THE PREFERRED EMBODIMENTS

The present invention involves a variety of fields of study and uniquely selected components that are developed for a compact inexpensive radiation-absorption spectroscopy gas-sensor apparatus. Absorption spectroscopy basically includes a waveguide for holding a gaseous specimen, while electromagnetic radiation (light) is passed into the container through the specimen and the. spectral wavelengths of the radiation emerging from the container are analyzed. The system can thus detect the presence of certain trace gases and determine their concentrations.

Waveguide

Figure 1:
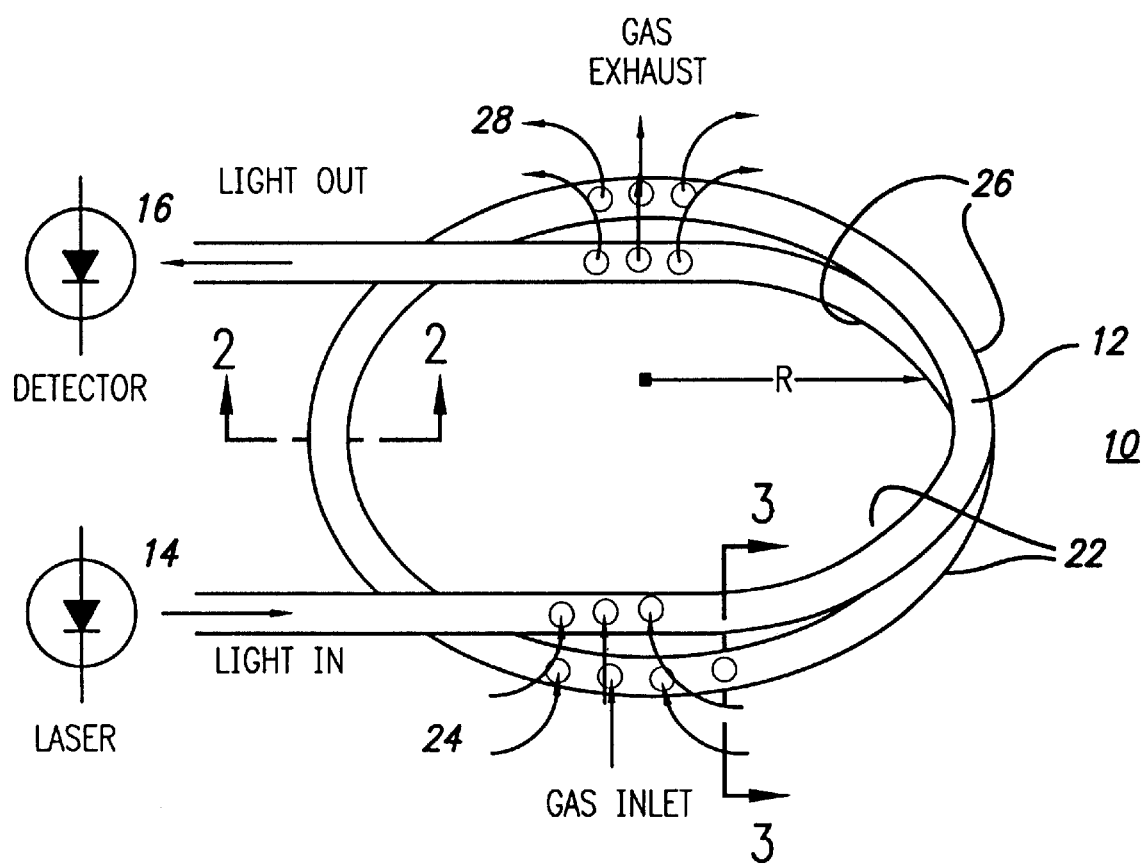
FIG. 1 is a top front perspective view of the waveguide of the present invention.
Figure 2:
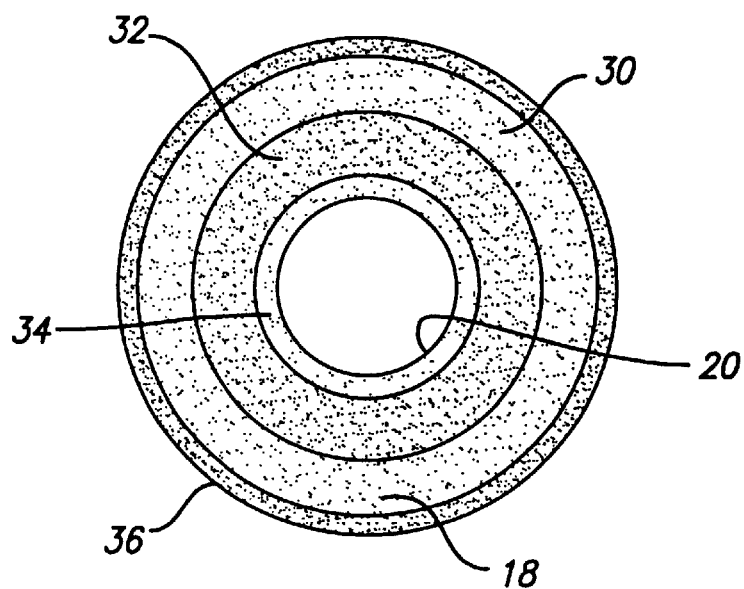
FIG. 2 is a sectional view taken along 2—2 of FIG. 1.
Figure 3:
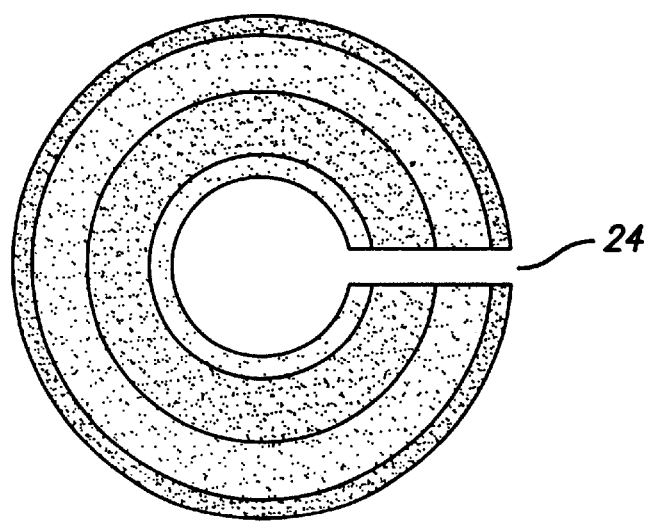
FIG. 3 is a sectional view taken along 3—3 of FIG. 1.

Referring first to FIGS. 1 through 3, the basic concept of absorption spectroscopy is schematically illustrated. A significant feature of the present invention is a perforated hollow waveguide 10 which serves simultaneously as the sample cell for containing a gaseous specimen for analysis, and as a light guide for directing a source of electromagnetic radiation through the specimen.

The waveguide includes a hollow elongated tube 12 with an inlet 14 and outlet 16, and a wall 18 with a smooth reflective inner surface 20 for guiding radiation along the interior of the tube. The tube is flexible, and for compact packaging is shaped (preferably by winding within an inside-flanged spool) into a generally oval or circular coil having a plurality of loops (1½ loops shown).

A first portion 22 of the loops of the waveguide includes perforated inlet openings 24, and a second portion 26 on the opposite side of the loops includes perforated exhaust openings 28. These openings serve for passage of the gaseous specimen through the wall, into the interior of the tube for analysis.

A pressure differential between the first portion 22 and the second portion 26 (see also FIG. 6) impels the gaseous specimen to quickly flow through the waveguide. In doing so, the gas passes along the plurality of half-loop paths (generally semicircular for a regular coil) between the inlet openings 24 and the exhaust openings 28 of each of the loops.

Light from an electromagnetic radiation source is coupled into the waveguide at the inlet 14 and detected at the outlet 16. As discussed later in detail, the detected signals are amplified, filtered and digitized; and the resulting signals are demodulated using a dedicated signal processor.

The plurality of half-loop paths between the inlet openings 24 and the exhaust openings 28 of each of the loops enable the gaseous specimen to almost instantly fill the waveguide for a quick response time. Yet the optical path of the radiation remains along the entire length of the waveguide for high sensitivity.

The length and the optical transmission losses determine the detection sensitivity of the waveguide. Flexible waveguides have been recently developed and improved for a variety of medical and industrial applications.

Plastic, metal and a variety of glass materials have been used as the base tube for the waveguide. Both leaky (index of refraction n >1) and attenuated-total-reflectance (n <1) waveguides have been fabricated using a combination of metallic films and dielectric coatings on the interior surface of the tube.

A schematic representation of the structure of a typical hollow waveguide of the present invention is shown in FIG. 2. The wall 18 is formed of a thin flexible silica glass capillary 30, having a metallic film 32 deposited on the inner surface of the glass, with a dielectric coating 34 deposited on the metallic film to provide the smooth reflective interior surface 20. The wall includes a polyimide outer jacket 36 to protect the tube from moisture, abrasion and other mechanical degradation.

The reflective metallic film 32 is preferably silver and the dielectric coating 34 is preferably silver iodide; however, certain applications may incorporate other materials. For example these may employ gold, copper, aluminum, nickel, platinum and zinc as the metallic film; with other dielectric coatings, e. g. magnesium oxide, silver bromide, copper iodide, silver sulfide, zinc sulfide and other suitable compounds. Selecting the dielectric/metallic films and controlling the relative coating thickness allows the waveguide loss to be minimal at the wavelength of interest.

Typical waveguide losses range from about 0.15 dB/m to 3 dB/m. Optical attenuation of waveguides has been studied in detail, and both experiment and theory show that the attenuation coefficient "α" scales according to $\alpha \sim 1/a^3$ and $\alpha \sim 1/R$, where a is the waveguide diameter, and R is the radius of curvature of a bend in the waveguide.

Waveguides can be of any size or curvature (provided that the diameter is small enough for effective bending) where size, weight and response time are not critical. For compact systems, however, the waveguide 10 preferably has a bore diameter of about 500 to 1000 micrometers ($\mu$m), and more preferably about 700 to 750 micrometers, with a typical glass outer diameter of about 950 $\mu$m, and a diameter of about 1050 $\mu$m including the outer jacket 36. Bore diameter can suitably range from about 250 to 2000 $\mu$m.

The bend radii R of about 5 cm have been established for compact packaging and can range up to about 20 cm and still provide relatively short multiple paths for the flow of the gaseous specimen through the waveguide. Even smaller bend radii are foreseeable with major improvements in materials and coatings.

The length of the waveguide 10 can be optimized for specific optical and wavelength requirements, and range from about 3 meters to about 20 meters. A preferable, versatile length of about 10 meters, having a coil with a bend radius of about 5 cm into about 31½ loops, appears suitable for many gas-sensor applications. These relations are based upon the well-known formula for finding circumference of a circle from its radius.

The size and quantity of the perforated openings 24 and 28 are balanced between maximizing gas flow while minimizing degradation of the physical and optical properties of the interior of the waveguide. A series of experiments with transmissometer data produced an empirical relationship relating the open area of the perforations to the cross sectional area of the waveguide.

A ratio of (330/3175), simplified as 0.104 or roughly 1/10, times the bore diameter of the waveguide was found to be a suitable relationship for the diameter of the perforated openings. It corresponds to perforated openings having a diameter of about 55 $\mu$m for a waveguide of 530 $\mu$m diameter.

Perforated openings as small as 10 $\mu$m, however, are considered to be commercially feasible, if desired, to maintain the maximum integrity of the wall of the guide. Response time is also influenced by the pressure differential between the first portion 22 and the second portion 26; however, flow through perforated openings having a diameter in the range of about 55 to 60 $\mu$m requires minimal pressure from an exhaust pump.

Consequently with about four perforations at each portion of a loop of the waveguide, there is almost no flow restriction and no additional optical losses associated with the waveguide. Response times, to gas-concentration changes, of less than a second are achieved.

Waveguide Performation Method

A preferred method of producing the perforated openings 24 and 26 in the waveguide 10 incorporates laser drilling. Some alternative methods of producing the perforated openings include chemical etching, is photolithography and electrostatic discharge.

Numerous experiments were conducted involving various laser-drilling parameters and techniques to produce perforated openings in fused glass capillaries, straight waveguides, and coiled waveguides.

Suitable perforated openings were produced using a $CO_2$ laser operating at 10.6 $\mu$m to perform the laser drilling. The laser output was modulated using a chopper, the output pulse duration was 50 milliseconds, and the peak power was nominally 7.5 watts.

The laser was focus ed to a spot size of about 50 $\mu$m and produced a perforated opening having a diameter of about 55 $\mu$m. Each perforation was completed with a single laser shot.

For high throughput processing, the laser drilling system can incorporate a $CO_2$ laser operating at up to 50 W, a free-beam laser-delivery system, computer-controlled target-motion-control hardware, and software to drive and coordinate the motion control and laser firing. The laser drilling process requires optimization to accommodate the properties of the specific waveguide being produced.

It was found that suitable perforated openings could be drilled in the capillary, the straight waveguide, and the complete coiled waveguide. The ability to perforate the outer jacket 36, the fused silica glass 30 and the internal metallic film 32 and coating 34 of the waveguide allows the drilling process to be performed at the end of the waveguide fabrication process.

In fact, the waveguide is preferably formed into the final coiled configuration, (as it would be-as assembled into a housing of a gas-sensor apparatus) and then drilled by the laser. This allows the process to be easily automated for efficient, robust production.

A preferred method for providing the waveguide 10 with the plurality of paths for flow of a gaseous specimen through the wall 18, includes the steps of: securing the waveguide into a coil, with the first portion 22 of loops and the second portion 26 of loops on opposed sides of the coil; laser drilling the perforated inlet openings 24 in the walls of the loops in the first portion; and laser drilling the perforated exhaust openings 28 in the walls of the loops in the second portion—whereby each of the plurality of perforated loops provides two generally semicircular paths for the gaseous mixture to flow from the inlet portion to the exhaust portion.

The above method more preferably includes about four perforated openings. Here each opening has a diameter of about 50 to 60 $\mu$m, in each portion of each loop.

The method can be altered in some applications having a range of about one to six openings, each having a diameter in a range from about 10 to 100 $\mu$m, in each portion of each loop. An alternative in other applications is to provide perforated openings only in selected loops of the coils.

It is also preferred that the laser drilling be directed radially outward, from within the coil, into the tube walls at the inner diameter of the loops of the waveguide. The walls at the inner diameter tend to retain any residual stress as compressive stress; whereas the outer diameters tend to retain any residual stress as tensile stress.

The wall of the waveguide adjacent the perforated openings is stronger in compression than tension. The openings in the walls at the inner diameter of the loops therefore are more resistant to subsequent stress fractures and are thus more durable.

To implement this strategy it is very highly desirable to drill through only just the inner-diameter wall of each loop. In other words, it is preferable to perforate the inner-diameter wall without penetrating the outer-diameter wall toward which the laser beam propagates as it passes through the inner-diameter wall. Preferably the beam never quite emerges from the near wall, the final increment of perforation being accomplished by thermal effects.

The single-wall drilling is thus achieved by limiting the laser pulse energy, to a level quickly found by a small amount of trial and error. Alternative methods include forming the perforated inlet openings and the perforated exhaust openings in the walls of the waveguide by chemical etching, or by photolithography, or by electrostatic discharge.

In addition, the desired gas transfer through the wall may instead be achieved using a wall whose bulk material is, or has been rendered, permeable to the subject gas or gases. In this approach it is important to bring to bear materials-science expertise to avoid impairment of the permeability by the reflective coating in the tube—and as well to avoid impairment of the reflectivity of the coating by any procedure used to attain permeability. That is, the reflective coating too must be either permeable in or removed from at least selected regions. As with the drilling technique, best results require careful choices of processing sequence—i.e., whether to provide permeability first and then metallize, or vice versa.

One advantage of a permeable-wall waveguide, or indeed a waveguide that provides gas passage via laser-drilled holes through the wall at intervals, is that a geometrically regular or orderly configuration (such as a coil) is not required to facilitate penetration. Thus in principle the waveguide can be dropped into a box in a very disorganized "crow's nest" or "spaghetti" fashion, and a median bulkhead then molded across the center of the box (with the stack of waveguide passing multiple times through the bulkhead).

The bulkhead thus separates the box into the desired gas-entry and gas-exhaust chambers. Entry and exhaust ports at corresponding opposite sides of the box complete the assembly.

The laser-drilling method, on the other hand, has several advantages in the forming of the perforated openings. Laser drilling is a direct process and requires no secondary operations, and is a dry process with virtually no resulting waste products.

The size of the perforated openings is easily controlled by adjusting the spot size of the laser beam on the surface of the waveguide. The process is well understood and requires little supporting equipment other than an arrangement of lenses or a delivery waveguide.

Perforations of the waveguide can be accomplished while the waveguide is premounted as a subassembly that can then be directly incorporated into the apparatus. The process of laser drilling is extremely fast, requiring only one or two laser shots per perforation.

Consequently many holes can be drilled in a short time. The ability to perforate the waveguide after it has been coated and looped is extremely beneficial and the result is a very low-cost process.

Absorption Spectroscopy Gas-Sensor Appartus

Figure 4:
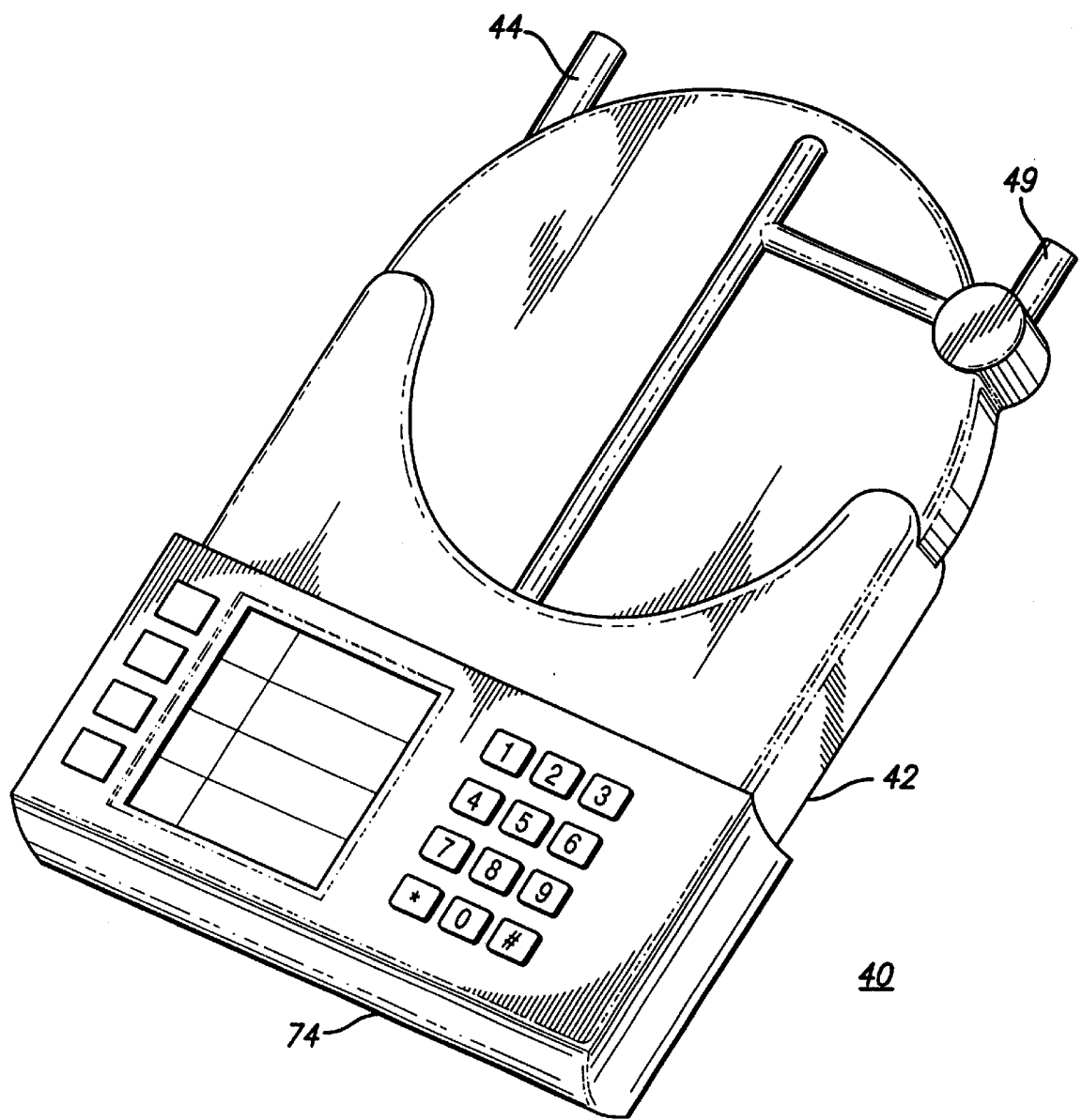
FIG. 4 is a top front perspective view of a handheld apparatus of the present invention.

Referring also to FIG. 4, a preferred embodiment of a handheld gas-sensor apparatus 40 is illustrated enclosed within a housing 42. The housing has dimensions of about 26 by 32 by 7.5 cm (10 by 12½ by 3 inches), which is quite compact in relation to other sensors with similar capabilities.

The weight of the apparatus in this configuration is about 3 kg (6½ pounds) including an internal battery power supply and case. The size and weight are readily manageable as a handheld gas-sensor apparatus. It is foreseeable that further design efforts will further reduce both the size and weight of the apparatus.

This handheld model of the gas-sensor apparatus has applications as an audit device in which periodic examination of a gas concentration is required. Because it is lightweight and handheld, a single individual can quickly and efficiently check the concentration in a number of locations. Such an apparatus is well suited to applications in the health care industry as well.

Figure 5:
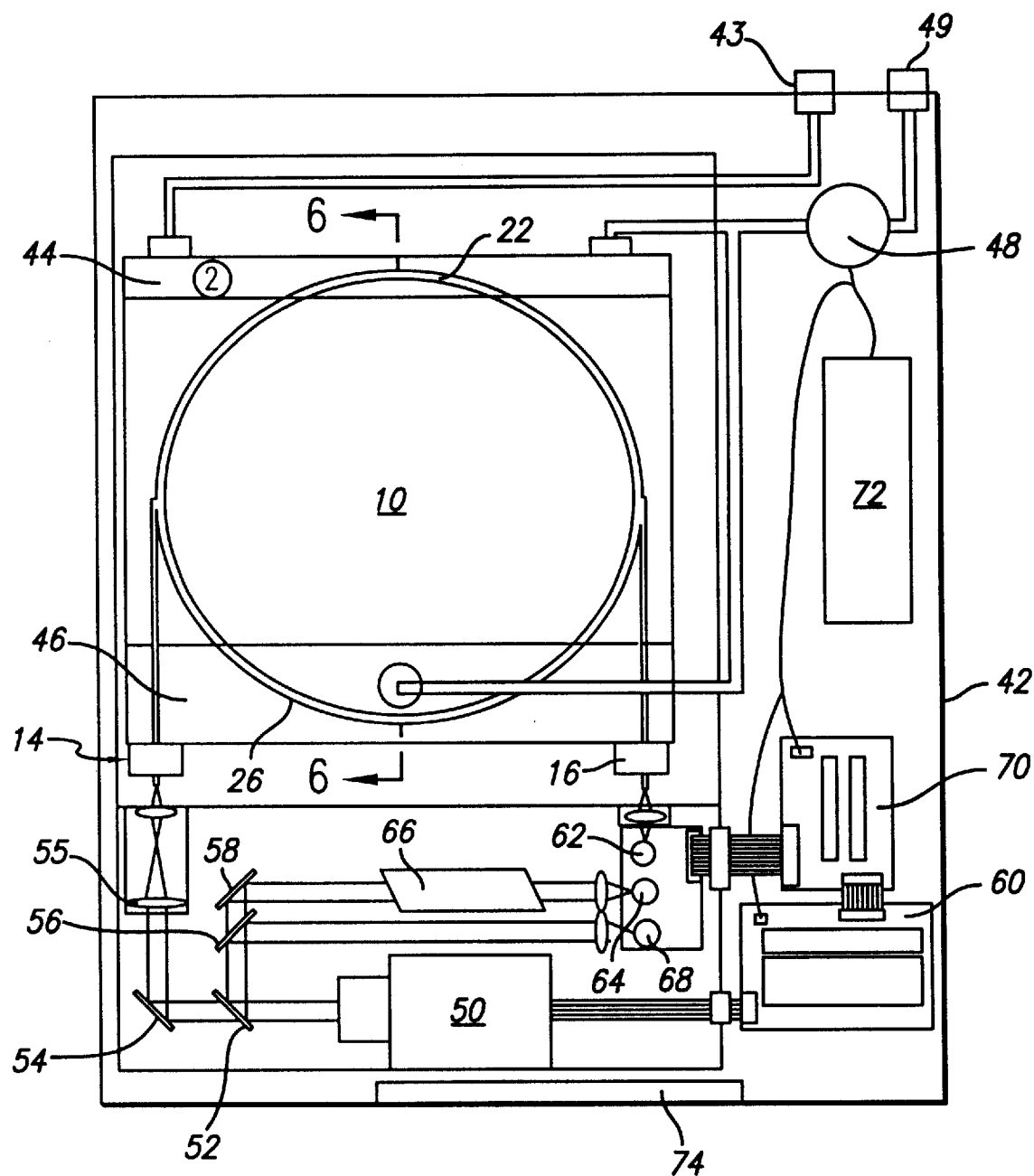
FIG. 5 is a top plan schematic view of the handheld apparatus of the present invention.
Figure 6:
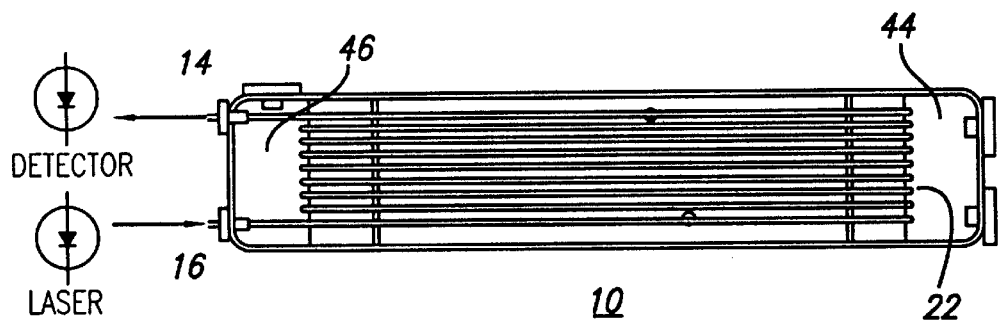
FIG. 6 is a sectional view taken along 6—6 of FIG. 5.

Referring also to FIGS. 5 and 6, a schematic layout shows the unique arrangement of compact components of this preferred embodiment of the gas-sensor apparatus 40 of the present invention. The components of the apparatus are arranged in a compact rectangular configuration and are enclosed within the housing 42. The perforated coiled waveguide 10 is arranged within the housing, to contain the gaseous specimen for analysis and to direct a source of electromagnetic radiation through the specimen. The waveguide includes a radiation inlet 14 adapted for receiving the radiation, and a radiation outlet 16 adapted for emitting the received radiation.

The housing 42 includes a gas entry conduit 43 leading into a gas entry chamber 44. The gas entry chamber encloses the first portion 22 of the waveguide and is adapted for receiving the gaseous specimen. The housing also includes a gas exhaust chamber 46 enclosing the second portion 26 of the waveguide and is adapted for exhausting the gaseous specimen.

The first portion of the waveguide is sealed within the inlet chamber, with the perforated gas-entry openings 24 in communication with the inlet chamber; and the second portion of the waveguide is sealed within the exhaust chamber with the perforated gas-exhaust openings 28 in communication with the exhaust chamber. Accordingly the gaseous specimen flows from the inlet chamber through the waveguide into the exhaust chamber.

A small exhaust pump 48 is connected to the exhaust chamber 46 to produce a pressure differential to evacuate the internal gases from the waveguide and the exhaust chamber and out through a gas exhaust conduit 49. The pressure differential draws the gaseous specimen into the inlet chamber 44, and through the numerous flow paths between the perforated inlet openings 24 and the exhaust openings 28, to fill the waveguide with the gaseous specimen for analysis. The pressure differential of the exhaust pump typically creates flow of about 20 cc/minute/opening through the waveguide.

An electromagnetic radiation source 50 is adapted, through a series of optical mirrors and lenses 52, 54, 55, 56, 58 for projecting electromagnetic radiation into the inlet 14 of the waveguide 10. The radiation source is typically a laser, preferably a semiconductor laser, and is actuated by a laser current supply and temperature controller 60.

A first radiation detector 62 is adapted for receiving radiation emitted from the outlet 16 of the waveguide. A suitable detector is an InGaAs PINs having an active area of 80 $\mu$m diameter, for wavelengths up to about 2 $\mu$m. An InSb detector is more suitable for wavelengths between 2 and 3 $\mu$m; and HgCdTe for wavelengths above 3 $\mu$m.

The series of lenses and mirrors includes a first 45° partially (about 20%) reflective mirror/beam-splitter 52, which allows most of the radiation to proceed to a second 45° reflective mirror 54 and through a focusing lens 55 into the inlet 14 of the waveguide. The radiation reflected by the first mirror 52 is directed to a third 45° partially (about 50%) reflective mirror/beam-splitter 56.

That unit 56 reflects about half of the radiation to a second detector 64—to detect variations in the laser output. Meanwhile the unreflected radiation proceeds to a fourth 45° reflective mirror 58, which reflects this radiation through a reference cell 66 to a third detector 68 for calibration of the radiation source 50.

Output signals from the detectors 62, 64, and 68 proceed to a signal processor 70. The processor analyzes the output signals of the detectors to identify and determine the concentration of specific trace gases within the gas specimen.

The apparatus is powered by an internal battery power supply 72. It is controlled and monitored by a keypad and display 74 on the upper surface of the housing 42.

RADIATION SOURCES AND DETECTORS

The radiation source 50 is selected for the wavelength(s) corresponding to the gas(es) to be detected and analyzed. The radiation source is typically any form of laser, and is preferably a semiconductor diode laser operating in the near-infrared (NIR), or alternatively a quantum cascade laser operating in the midinfrared (MIR). Both types of semiconductor lasers offer single-longitudinal-mode performance and wide tuning ranges, with tuning controlled by temperature and injection current.

Various semiconductor lasers are commercially available, covering a wide spectrum. Some examples of semiconductor lasers of wavelength about 1 to 3 $\mu$m include AlGaAs, InGaAs P/InP, GaInAg Ab/AlGaAs/Sb, and from about 3 to 13 $\mu$m by the use of quantum cascade lasers.

Quantum cascade (QC) lasers have been in development since 1994 and high-power, room-temperature QC lasers are becoming commercially available in many wavelengths. QC lasers operate on a different principle from that of diode lasers. The QC devices are typically fabricated of a cascaded gallium indium arsenide/aluminum indium arsenide (GaInAs/AlInAs) multiple quantum lattice—matched to an indium phosphate (InP) substrate.

When an electric current flows through the laser, electrons cascade down an energy staircase; every time they hit a step they emit an infrared photon. The emitted photons are reflected back and forth between built-in mirrors, stimulating other quantum jumps and the emission of other photons.

The QC laser can be tailored to emit light at a specific wavelength set at nearly any point over a very wide range of the infrared spectrum. This is done in the manufacturing process by simply varying the thickness of the layers, using the same combination of materials.

A more detailed discussion of QC lasers appears in technical publications of Bell Labs. Another source is presentations and publications by Bell Labs at the 1998 meeting of the American Association of the Advancement of Science (AAAS) in Philadelphia, Pa.

The spectral ranges of QC lasers, the infrared wavelength regions from 3 to 5 $\mu$m and 8 to 13 $\mu$m, are important for such applications as pollution monitoring, and industrial process control for environmentally safe manufacturing, because many hazardous and toxic chemicals have optical absorption "fingerprints" at these wavelengths. As the QC laser device matures it will add to the number of gases that can be measured with absorption spectroscopy technology. The use of QC devices may also improve sensitivities since many molecules exhibit stronger absorption in the midinfrared.

The detectors 62, 64 and 68 of the gas-sensor apparatus suitably use InGaAs photodetectors to address wavelengths up to 2 $\mu$m. The telecommunication industry has driven the development of room-temperature InGaAs detectors to provide high responsivity and bandwidth detection in the NIR. Detectors for wavelengths of 2 to 3 $\mu$m suitably use InSb photodetectors to enable room-temperature operation. Detectors for wavelengths between 3 to 6 $\mu$m and higher typically require the use of thermoelectrically (TE) cooled HgCdTe detectors to yield low-concentration trace gas detection. Multistage TE cooled devices are available as off-the-shelf technology, although they are significantly more expensive than the room-temperature InGaAs detectors. The primary spectral regions of interest are addressable ii with solid-state electronics technology and do not require cryogenic operating temperature.

RACK-MOUNTED GAS-SENSOR APPARATUS

Depending on the application, the gas sensor 40 can be handheld and battery operated or it can be a conventional rack-mounted gas-sensor apparatus operating on standard AC power.

Figure 7:
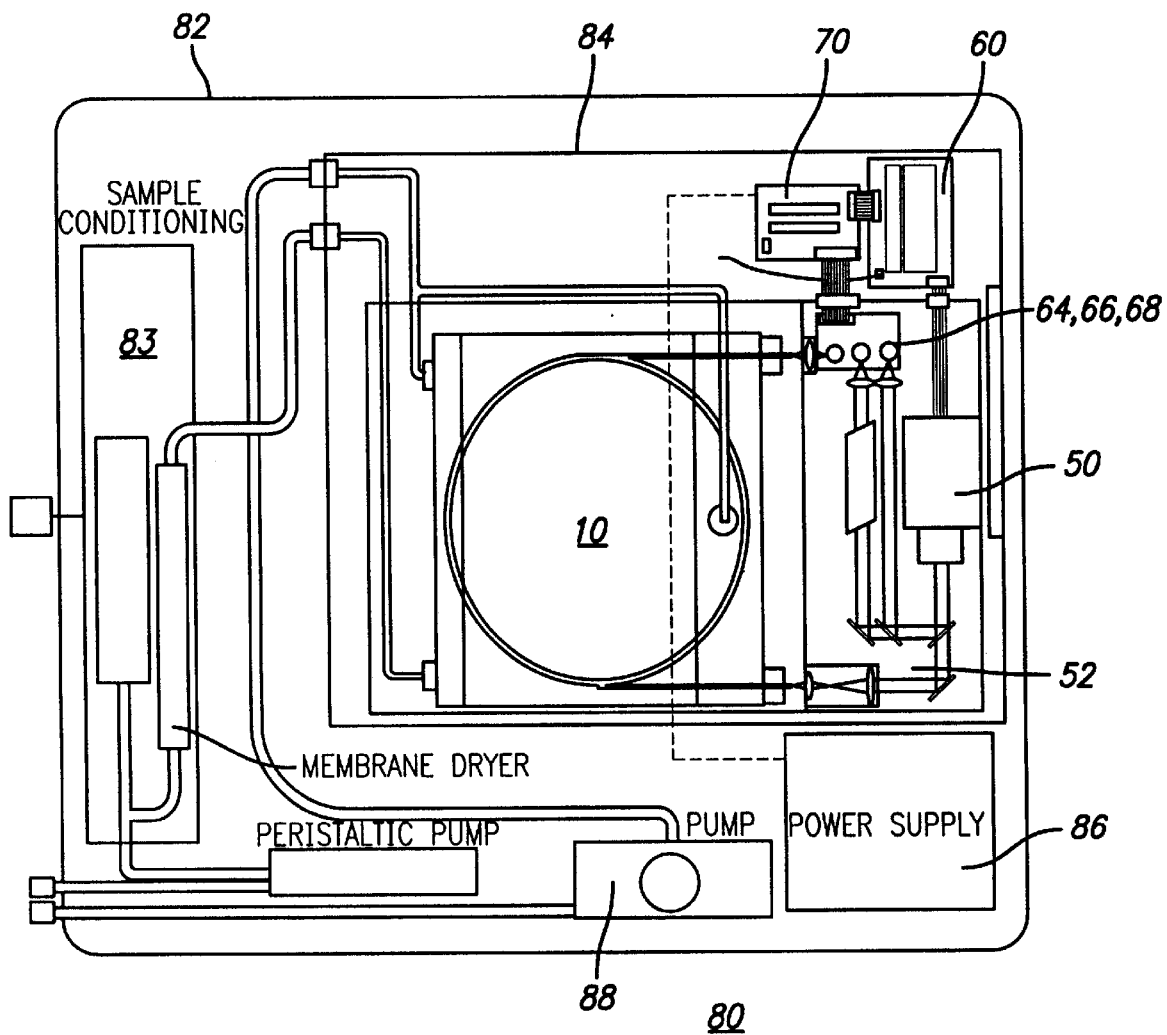
FIG. 7 is a top plan schematic view of a rack-mounted apparatus of the present invention, particularly for use in removing water vapor from the gas specimen preparatory to analysis.

Referring also to FIG. 7., another embodiment of a gas-sensor apparatus 80 is schematically illustrated packaged to be rack-mounted, rather than handheld. The gas-sensor apparatus 80 is also quite compact and functions similarly to the handheld apparatus 40; however, the components are packaged into a rugged industrial housing 82 adapted to fit a conventional 48 cm (19 inch) rack.

The rack mounting, in conjunction with some ancillary conditioning hardware 83, makes the apparatus suitable for an extractive process measurement. The apparatus includes the same configuration of waveguide 10, radiation source 50, optics 52, detectors 64, 66 and 68, laser controller 60, signal processor 70 (as described in reference to the handheld embodiment of FIG. 5), all enclosed within an internal enclosure 84.

The internal enclosure includes the same configuration of gas inlet chamber 44 and exhaust chamber 46 (as described in reference to housing 42 of FIG. 5). A larger-capacity a. c. power supply 86 and exhaust pump 88 are arranged within the industrial housing 92 to accommodate the power and flow requirements of the sample conditioning hardware.

The extra capacity of this embodiment also allows multiple gas sensors in a single cabinet. Also, because the flow requirements of the gas-sensor apparatus are small, sample conditioning such as water vapor removal is greatly simplified (in comparison to prior-art systems in place today). Consequently, sample conditioning and multiple gas measurements can be accomplished in a single 48 cm rack-mounted instrument.

Process control applications are readily monitored by the rapid response of the gas-sensor apparatus. The lightweight, compact design also facilitates gas-sensor applications requiring installations in close proximity to the process to be monitored.

Wavelength Modulation Spectroscopy

The specific spectroscopic approach used in the gas sensor of the present invention is wavelength modulation spectroscopy. Diode lasers are particularly advantageous and have low sensitivity to laser output, tuning parameters, high spectral selectivity for interference rejection, synchronous demodulation for sensitive detection limits, and simplicity in terms of achieving the required modulation and demodulation.

In certain situations a single gas-sensor apparatus can be configured to monitor multiple species. This is easily accomplished where the species to be measured have absorption bands that lie within the tuning range of the laser. For example, a laser that operates at 1.542 $\mu$m can easily measure $NH_3$, $CO_2$, and $H_2O$ vapor simultaneously.

Figure 8:
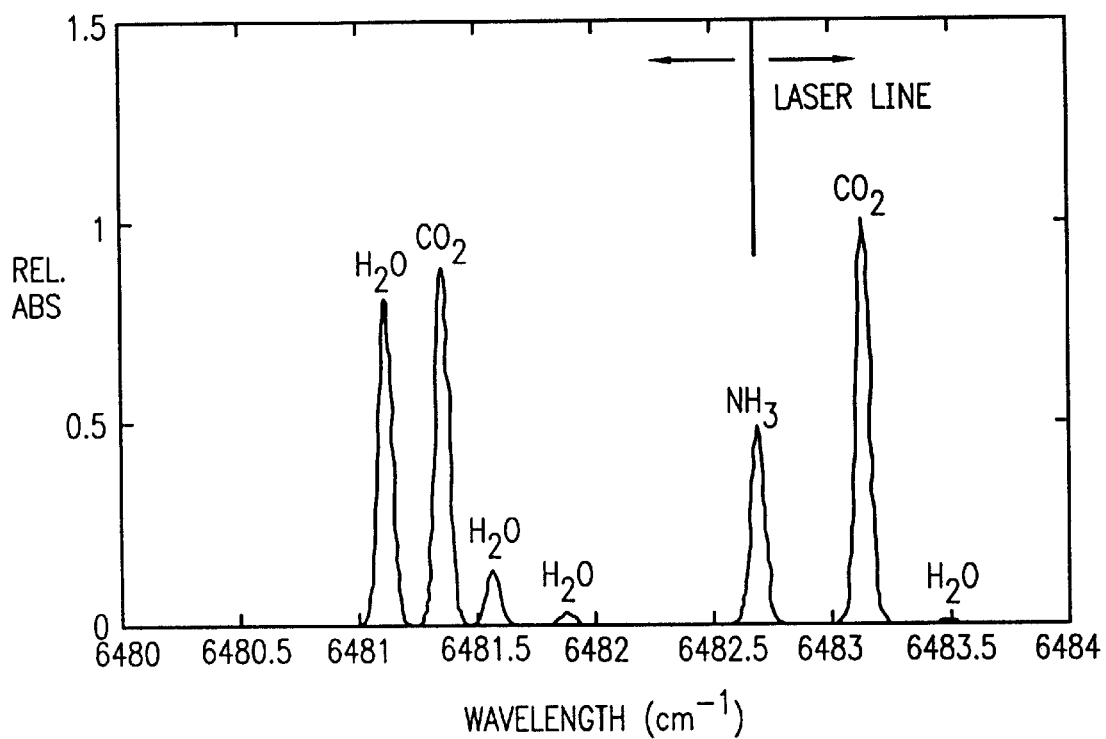
FIG. 8 is a spectrum of absorption bands of water, carbon dioxide and ammonia for detection.

In FIG. 8, several absorption lines are plotted for water vapor, carbon dioxide and ammonia as a function of wavelength. The diode laser is tuned first to the peak of an absorption line corresponding to ammonia. A measurement of the ammonia concentration is made.

The laser is then tuned to a $CO_2$ line and its concentration is determined. Finally the water vapor concentration is determined. The process is then repeated to provide continuous monitoring of each species. Should the spectral features of the gases overlap it is necessary to delay the concentration determination until the laser has been tuned to all three lines. The solution for the three concentrations is simply a matter of simultaneously solving a set of three linear equations.

For diode lasers operating at these wavelengths, typical tuning-range capabilities are approximately 2 nm. Several new laser devices have been recently introduced that can provide up to 50 nm of tuning and future developments will likely increase tuning ranges. The wider tuning ranges provide access to a larger number of gases that could be measured simultaneously.

The minimum detection capability of the gas-sensor apparatus depends upon the absorption strength of the particular molecule of interest and upon transmission losses in the waveguide. Thus reducing those losses is an important factor in improving the performance of the gas sensor. This work has shown that minimizing transmission losses by depositing smooth waveguide coatings, in some significant cases, is more important than making lengthy sections in the interest of improving signal through longer gas-absorption lengths.

Although ideally a waveguide of specific length can be associated with each gaseous specimen, the invention contemplates that a single length of waveguide will suffice in handling a large variety of gases—with no necessity for tailoring the waveguide length to the application. From a production point of view, this is an extremely beneficial feature.

Electronics System

The electronics system provides interaction of a keypad and display 74 with the controller 60, and performs gas-detection analysis within the signal processor 70. Although the electronic system is designed for the apparatus, it is based upon conventional technology and is not illustrated in detail, but is described in terms of the general function of the system.

The electronics system includes an electronic subsystem including a mezzanine interface board (MIB); and a processor subsystem including a digital signal processor (DSP) board, and signal-processing software.

The ELECTRONICS SUBSYSTEM includes the MIB, the keypad and display, system power supply and the various cables required to interconnect the various components.

The MIB contains five analog to digital converters (ADCs). Three channels are dedicated to the signals coming from the detectors 62, 64, 68 in the optical system, and a fourth channel provides a modulation reference signal. A separate ADC is used for multiple input devices to digitize several channels of slowly varying process signals associated with the laser current and temperature controllers (60) as well as thermal and pressure transducers.

The outputs of the sample-and-holds are into sixteen-bit ADCs capable of handling 100 kHz sample rates. This technology has been developed extensively for the audio compact-disc industry and consequently represents high-technology reliability and low component cost. A sinusoid wave generator IC is used to provide the required modulation of the laser diode 50 about 10 kHz).

Also included on the MIB board are several digital to analog converters (DACs) for outputting voltages to control the various hardware components. The remaining components in the electronics subsystem are standard commercial off-the-shelf components and warrant little discussion.

The gas analyzer has been designed to enable operation of the apparatus from a single conventional modular 12 V power supply.

The PROCESSOR SUBSYSTEM (Hardware) is made up primarily of the DSP processor board. The core of the DSP board is an Analog Devices ADSP-21062L ("SHARC") DSP. The SHARC unit is a floating-point DSP processor with an instruction pipeline and instruction cache. Additional DRAM (6 Mbyte) and nonvolatile flash memory (1 Mbyte) are connected to the external bus of the SHARC. The DRAM allows instructions to be executed directly from external memory, or for floating point data to be stored. The flash memory is used to store the code to boot up the SHARC and is also used to store data that will persist after the power-off.

Two MAX3100 UARTs are connected to the SHARC via synchronous serial ports (SPORTs). Each UART is used to drive an RS232 or RS485 interface, which allows the DSP board to communicate to various devices including ADCs, DACs, microcontrollers, or a PC serial port if desired.

Software algorithms and source code were developed to implement harmonic-detection lock-in amplifiers, used to demodulate and filter the signals from the detectors. The lock-ins are implemented in software using standard DSP techniques on the SHARC.

Markets and Applications

Many industries need to monitor the air within their facilities or to monitor the effluents escaping into the environment. Often the requirements are for periodic monitoring of a source or an atmosphere for safety or production issues. The infrastructure associated with a conventional analyzer is either not cost effective or prohibitive on a space-allocation basis.

Examples of these industries are the power generation (NO, $SO_2$, $NH_3$, CO, $CO_2$, $H_2O$), semiconductor (HF, $O_2$, $H_2O$, $O_3$) and petroleum (NO, CO, $CH_4$, BTX and other VOCs) industries as well as the aluminum (NO, HF), fertilizer (NO, $NH_3$, CO, $CO_2$) and natural-gas producers. Each of these industries has periodic as well as continuous monitoring requirements to assure that processes are running correctly.

Because of the wide range of gases that can be measured, many different industries can be addressed with the gas-sensor apparatus of the present invention. In each case they are interested in monitoring gases to improve their product and to comply with regulations.

The use of NO is attracting major attention in the medical field for a wide variety of treatments and diagnosis. For example, the 1998 Nobel Prize in Medicine was awarded to Furchgott, Ignarro and Murad for their discoveries concerning "nitric oxide as a signaling molecule in the cardiovascular system". NO is being used to treat or diagnose heart disease, shock, blood disease, lung diseases such as asthma and others and even gastrointestinal ailments.

Whether administered as a treatment or monitored as a marker, the NO involved will have to be monitored. NO exhibits a relatively weak absorption at 1.794 $\mu$m and is readily adapted to the gas-sensor apparatus. In these applications quick response times and low detection limits as provided by the apparatus of the present invention are often important.

Competitive Advantages

There are numerous advantages to the absorption spectroscopy technology and the gas-sensor apparatus of the present invention. First, the level of sensitivity is superior to competing technologies. Secondly, the plurality of parallel gas flow paths of the present invention provides quick response time over other types of sensors.

In addition, the handheld apparatus 40 allows operators to cover more physical space in the same amount of time with the gas-sensor apparatus, for increased safety and productivity. The gas-sensor apparatus is made up essentially of all solid-state components for increased durability and reliability; the apparatus is well suited to industrial field deployment and has a long service life.

In rack-mounted applications the sensor size, weight, power and flow requirements are small. The instrument can be placed in close proximity to the point of measurement. Sample-conditioning requirements are greatly reduced by the low flow requirement.

These factors greatly reduce the costs associated with an installation of the sensor in comparison to other technologies. Finally, because the sensors can be packaged in relatively small volumes, multiple gas measurements are possible in a single compact enclosure.

The preferred embodiments provide a novel waveguide and optical gas-sensor apparatus that is physically compact, lightweight and durable. The gas-sensor apparatus is extremely sensitive, with low minimum detection limits for trace gases, and has a rapid response time. The gas sensor is also accurate, reliable and relatively very inexpensive in comparison with prior-art technology. In view of these many advantages the invention is believed to represent an unusually worthwhile advance in the art.

It will be understood that the foregoing disclosure is intended to be merely exemplary, and not to limit the scope of the invention—which is to be determined by reference to the appended claims.

What is claimed is:

1. A waveguide for holding a gaseous specimen for spectral analysis; the waveguide comprising:
    a hollow elongated tube, having an interior with inside diameter of two millimeters or less, a radiation inlet and a radiation outlet therein, and having a wall with a substantially smooth reflective inner surface adapted for guiding radiation along the interior thereof; and
    means for passage of the gaseous specimen through the wall into the interior of the tube; said passage means comprising:
        a first portion of the tube, having at least one perforated opening through the wall thereof, adapted for receiving the gaseous specimen therein; and
        a second portion of the tube, having at least one perforated opening through the wall thereof, adapted for exhausting the gaseous specimen therefrom;
    wherein the tube is curved into a compact configuration having at least one continuously communicating internal segment that extends between the first portion and the second portion; and
    wherein the compact configuration is a coil having at least one complete loop, and the first portion and the second portion are on opposed sides of the coil, whereby the tube is adapted to provide a plurality of paths for the gaseous specimen to flow therein.

2. The waveguide of claim 1, further comprising:
    a housing supporting the tube and having a gas entry chamber enclosing the first portion of the tube adopted for receiving the gaseous specimen therein, and having a gas exhaust chamber enclosing the second portion of the tube and adapted for exhausting the gaseous specimen therefrom.

3. The waveguide of claim 1, wherein:
    the inside diameter is in a range of about 250 to 2000 $\mu$m and a length in a range of about three to twenty meters;
    the coil has a radius of curvature in the range of about five to twenty centimeters and a number of loops in a range of about eight to sixty-five;
    in the first portion, each of the loops has at least one perforated opening therein, of diameter in a range of about ten to one hundred micrometers; and
    in the second portion, each of the loops has at least one perforated opening therein, of diameter in the range of about ten to one hundred micrometers.

4. The waveguide of claim 1, wherein:
    the inside diameter is about one-half millimeter;
    the tube has a length of about ten meters;
    the coil has a radius of about five centimeters and about thirty-one and a half loops; and
    in both the first portion and the second portion each of the loops has a plurality of perforated openings of diameter about fifty micrometers.

5. An apparatus for detecting and determining a concentration of at least one gas within a gaseous specimen by radiation-absorption spectroscopy; said apparatus comprising:
    a coiled hollow waveguide having a radiation inlet and a radiation outlet therein, and having an interior, and being adapted for guiding radiation along the interior;
    means for providing a plurality of paths for flow of the gaseous specimen within the waveguide;
    means for projecting radiation along the interior of the waveguide to irradiate the gaseous specimen; and
    means for analyzing the radiation emerging from the gaseous specimen to detect and determine the concentration of at least one gas in the specimen;
    wherein the means for providing a plurality of paths comprise the coiled waveguide having at least one complete loop, with a first portion of each loop and a second portion of each loop at opposed sides of the coiled waveguide, and the first portion having at least one perforated opening for receiving the specimen, and the second portion having at least one perforated opening for exhausting the specimen;
    whereby the plurality of paths comprise two half-loop paths across each loop, respectively; and
    the second portion having an exhaust pump for exhausting the specimen, thereby impelling flow of the specimen through the waveguide.

6. The apparatus of claim 5, wherein:
    the projecting means comprise a laser disposed to project radiation into the inlet of the waveguide.

7. The apparatus of claim 6, wherein:
    the laser comprises a semiconductor diode laser.

8. The apparatus of claim 6, wherein:
    the laser comprises a semiconductor quantum cascade laser.

9. The apparatus of claim 5, wherein the analyzing means comprise:
    a photodiode disposed to receive the radiation emitted from the outlet of the waveguide; and
    signal processing means for analyzing the output of the photodiode.

10. The apparatus of claim 5, further comprising:
    means for displaying the output of the analyzing means; and
    means for control of operation of the apparatus by an operator.

11. The apparatus of claim 10 wherein:
    the displaying means and the control means are adapted for operation at a location remote from the source of the gaseous specimen.

12. An apparatus for detecting and determining a concentration of plural respective specific gases within a gaseous mixture specimen; said apparatus comprising:
    a hollow waveguide formed in a coil and having a radiation inlet and a radiation outlet therein, and having an interior, and being adapted for guiding radiation along the interior;
    discrete inlet- and outlet-chamber defining means at respective separated segments of the coil for providing a plurality of paths for flow of the gaseous specimen within the waveguide;
    means for sensing and recording spectra for the plural specific gases of the gaseous specimen;
    means for projecting radiation along the interior of the waveguide, to be absorbed by each of the plural specific gases therein; and
    means for analyzing the radiation emerging from the gaseous specimen.

13. The apparatus of claim 12, wherein:
    the projecting means comprise a tunable laser for projecting radiation into the inlet of the waveguide.

14. The apparatus of claim 13, wherein:
the projecting means comprise a semiconductor diode laser.

15. The apparatus of claim 13, wherein:
the projecting means comprise a semiconductor quantum cascade laser.

16. The apparatus of claim 13, wherein:
the plural respective gases include at least one of $NH_3$, $CO_2$ and $H_2O$; and
the laser is tunable within the near-infrared spectrum at about 1.54 $\mu$m.

17. The apparatus of claim 12, wherein:
the plural respective specific gases within the gaseous mixture specimen includes at least one of the following gases: $NH_3$, $CO_2$, $CH_4$, $H_2O$, and NO.

18. The apparatus of claim 12, wherein:
the plural specific gases within the gaseous mixture specimen includes at least one of the following gases: NO, $NO_2$, $SO_2$, $NH_3$, CO, $CO_2$, and $H_2O$.

19. The apparatus of claim 12, wherein:
the plural specific gases within the gaseous mixture specimen includes at least one of the following gases: HF, $O_2$, $H_2O$, and $O_3$.

20. The apparatus of claim 12, wherein:
the plural specific gases within the gaseous mixture specimen includes at least one of the following gases: NO, $NO_2$, $CH_4$, BTX and VOCS.

21. A handheld self-contained portable apparatus for detecting and measuring at least one gas within a gaseous specimen by radiation-absorption spectroscopy, the apparatus being for use with a portable source of energy for powering the apparatus; said apparatus comprising:
a coiled waveguide having a radiation inlet and a radiation outlet, and having an interior, and being adapted for guiding radiation along the interior;
means for providing flow of the specimen within the interior of the waveguide;
means for projecting radiation along the interior of the waveguide to irradiate the gaseous specimen;
means for analyzing the radiation emerging from the gaseous specimen to detect and determine the concentration of at least one gas in the specimen;
housing means for enclosing the waveguide, the projecting means, the analyzing means, the path-providing means and the flow-providing means;
wherein the housing means comprise a housing supporting the waveguide in coiled loops, the housing having an inlet chamber enclosing a first portion of the loops and receiving the gaseous specimen therein, and having an exhaust chamber enclosing a second portion of the loops and exhausting the gaseous specimen therefrom;
means for controlling the apparatus; and
means for displaying the analysis of the apparatus.

22. The Appartus of claim 21, having overall dimensions not exceeding about twenty-five centimeters by thirty centimeters by eight centimeters.

23. The apparatus of claim 21, having a weight not exceeding about three kilograms.

24. The apparatus of claim 21, wherein:
the projecting means comprise a laser adapted to project radiation into the inlet of the waveguide; and
the analyzing means comprise a photodiode adapted to receive the radiation emitted from the outlet of the waveguide, and signal processing means adapted for analyzing the output of the photodiode.

25. A method for adapting an elongated hollow waveguide having a wall and an interior, for a plurality of paths of flow of a gaseous specimen through the wall; said method comprising the steps of:
securing the waveguide into a coil having at least one loop, with a gas entry portion of each loop and a gas exhaust portion of each loop at opposed sides of the coil;
forming at least one perforated opening through the wall of substantially each loop in the entry portion for entry of the gaseous specimen; and
forming at least one perforated opening through the wall of substantially each loop in the exhaust portion for exhaust of the gaseous specimen;
whereby substantially each perforated loop provides two half-loop paths for the gaseous mixture to flow from the entry portion to the exhaust portion.

26. The method of claim 25, wherein:
the forming step comprises the step of laser drilling.

27. The method of claim 25, wherein:
the forming step comprises the step of chemical etching.

28. The method of claim 25, wherein:
the forming step comprises the step of photolithography.

29. The method of claim 25, wherein:
the forming steps comprise the step of electrostatic discharge.

30. The method of claim 25, wherein:
the forming step comprises forming the perforated openings having a diameter about one-tenth the inner diameter of the waveguide.

31. A waveguide produced by the method of claim 25.

32. The waveguide of claim 31, having an inside diameter of about one-half millimeter and perforated openings of diameter about fifty micrometers.

33. An apparatus for detecting and measuring at least one gas within a gaseous specimen by radiation-absorption spectroscopy; said apparatus comprising:
a housing;
an elongated coiled hollow flexible waveguide arranged within the housing and having a wall, an interior, a radiation inlet therein adapted for receiving radiation, and a radiation outlet therein adapted for emitting the received-radiation;
the housing having a gas entry chamber enclosing a first portion of the waveguide and adapted for receiving the gaseous specimen; and having a gas exhaust chamber enclosing a second portion of the waveguide and adapted for exhausting the gaseous specimen; wherein the first portion and the second portion are on opposed sides of the coiled waveguide;
the first portion including part of at least one loop of the waveguide and having at least one perforated opening defined therein, whereby the interior thereof is in communication with the inlet chamber; and the second portion including part of at least one loop of the waveguide and having at least one perforated opening defined therein, whereby the interior thereof is in communication with the exhaust chamber; wherein the gaseous specimen flows from the inlet chamber, through the waveguide, into the exhaust chamber;
an exhaust pump connected to the exhaust chamber for providing flow of the specimen through the waveguide;
a radiation source adapted for projecting electromagnetic radiation into the inlet of the waveguide;

a radiation detector adapted for receiving the radiation emitted from the outlet of the waveguide; and a signal processor for analyzing the output of the detector to identify and determine the concentration of at least one gas within the gas specimen.

34. A waveguide for holding a gaseous specimen for spectral analysis; the waveguide comprising:

a hollow elongated tube, having an interior with inside diameter of two millimeters or less, a radiation inlet and a radiation outlet therein, and having a wall with a substantially smooth reflective inner surface adapted for guiding radiation along the interior thereof, and formed into at least one loop; and means for defining separate, discrete intake and exhaust regions, spaced apart along the loop, for passage of the gaseous specimen through the wall into and out from, respectively, the interior of the tube.

35. A waveguide for holding a gaseous specimen for spectral analysis; the waveguide comprising:

a hollow elongated tube, having an interior, a radiation inlet and a radiation outlet therein, and having a wall with a substantially smooth reflective inner surface adapted for guiding radiation along the interior thereof; and means for defining separate, discrete intake and exhaust regions for passage of the gaseous specimen through the wall into and out from, respectively, the interior of the tube; said regions comprising:

a discrete group of multiple intake perforations formed through the waveguide wall, along a corresponding discrete intake segment of the waveguide, and a discrete group of multiple exhaust perforations, distinct from the intake perforations, formed through the waveguide wall along a corresponding discrete exhaust segment of the waveguide; and wherein the longitudinal paths extend within the waveguide from the intake perforations to the exhaust perforations.

36. The apparatus of claim 35, wherein:

each discrete group of perforations extends along only a respective discrete segment of the waveguide; and in the aggregate all said respective segments occupy no more than one-eighth the total length of the waveguide.

37. The apparatus of claim 35, wherein:

each discrete group of perforations extends along only a respective discrete segment of the waveguide; and in the aggregate all said respective segments occupy no more than approximately one percent, or less, of the total length of the waveguide.

38. The apparatus of claim 35, further comprising:

means for minimizing radiation leakage from the waveguide in comparison with radiation propagation distance along the waveguide interior; wherein:

each discrete group of perforations extends along only a respective discrete segment of the waveguide; and the leakage-minimizing means comprise restriction of the aggregate of all said respective segments to occupy only a fraction of the total length of the waveguide.

39. The apparatus of claim 35, further comprising:

means for minimizing radiation leakage from the waveguide in comparison with radiation propagation distance along the waveguide interior; wherein:

each discrete group of perforations extends along only a respective discrete segment of the waveguide; and the leakage-minimizing means comprise limitation of the aggregate of all said respective segments to occupy no more than one-eighth the total length of the waveguide.

40. A waveguide for holding a gaseous specimen for spectral analysis; the waveguide comprising:

a hollow elongated tube, having an interior, a radiation inlet and a radiation outlet therein, and having a wall with a substantially smooth reflective inner surface adapted for guiding radiation along the interior thereof;

said tube being arranged to form a coil or other configuration; and a bulkhead that segregates sectors of the coil or configuration into separate, discrete intake and exhaust regions for passage of the gaseous specimen through the wall into and out from, respectively, the interior of the tube.

41. The waveguide of claim 40, wherein:

spectral-analysis sensitivity, in terms of radiation propagation distance within the waveguide, is established by a pathlength through substantially the entire length of the tube; but response time, in terms of changeover of gas within the waveguide to fluctuations of gaseous-component concentrations in the specimen, is controlled by pathlengths through, and pressure differential applied across, not the entire length of the tube but substantially only the distance within the tube between the intake and exhaust regions, which in the case of a coil is the length of one half-loop of the coil;

whereby selection of pressure and a controllably high ratio of entire tube length to distance between intake and exhaust regions optimizes both sensitivity and response time.

42. An apparatus for detecting and determining a concentration of at least one gas within a gaseous specimen by radiation-absorption spectroscopy; said apparatus comprising:

a hollow waveguide formed in a coil and having a radiation inlet and a radiation outlet therein, and having an interior, and being adapted for guiding radiation along the interior;

discrete inlet- and outlet-chamber defining means at respective separated segments of the coil for forcing multiple portions of the gaseous specimen to flow along respective multiple discrete longitudinal paths within the waveguide interior, as distinguished from diffusion of gas in and out of the waveguide interior;

is means for projecting radiation along the waveguide interior to irradiate the gaseous specimen; and means for analyzing the radiation emerging from the gaseous specimen to detect and determine the concentration of at least one gas in the specimen.

43. An apparatus for detecting and determining a concentration of at least one gas within a gaseous specimen by radiation-absorption spectroscopy; said apparatus comprising:

a hollow waveguide formed in a coil and having a radiation inlet and a radiation outlet therein, and having an interior, and being adapted for guiding radiation along the interior;

means for forcing multiple portions of the gaseous specimen to flow along respective multiple discrete longitudinal paths within the waveguide interior, as distinguished from diffusion of gas in and out of the waveguide interior;

means for projecting radiation along the waveguide interior to irradiate the gaseous specimen;

means for analyzing the radiation emerging from the gaseous specimen to detect and determine the concentration of at least one gas in the specimen;

a discrete group of intake perforations formed through the waveguide wall, along a corresponding discrete intake segment of the waveguide coil; and a discrete group of exhaust perforations, distinct from the intake perforations, formed through the waveguide wall along a corresponding discrete exhaust segment of the waveguide coil;

wherein the longitudinal paths extend within the waveguide from the intake perforations to the exhaust perforations.

44. The apparatus of claim 43, wherein:

the forcing means comprise a pump.

45. The apparatus of claim 43, wherein:

the forcing means comprise means for applying a pressure differential across the plural paths.

46. The apparatus of claim 43, wherein:

each discrete group of perforations extends along only a respective discrete segment of the waveguide; and in the aggregate said respective segments occupy no more than one-eighth the length of the waveguide.

47. The apparatus of claim 46, wherein:

the forcing means comprise means for applying a pressure differential between the intake and exhaust perforations.

48. The apparatus of claim 43, wherein:

the forcing means provide sufficiently rapid gas changeover within the waveguide to achieve apparatus response time of approximately one second, or faster, to concentration fluctuations in the specimen.

49. An apparatus for detecting and determining a concentration of plural respective specific gases within a gaseous mixture specimen; said apparatus comprising:

a tunable laser selectively providing radiation of plural wavelengths for use in monitoring plural gases;

a hollow waveguide formed in a coil and adapted for guiding radiation along an interior of the waveguide and having:

an inlet for radiation from the tunable laser, said inlet having substantially no conical radiation coupler, and a waveguide interior with inside diameter of two millimeters or less, and radius of curvature equal to approximately five centimeters, or more, at substantially all points along the waveguide, and an outlet for radiation from the tunable laser after passage along the waveguide, said outlet having no conical radiation coupler;

discrete inlet- and outlet-chamber defining means at respective separated segments of the coil for providing multiple substantially parallel and discrete paths for directed flow of the gaseous specimen longitudinally within the waveguide interior;

means for projecting the laser radiation into the radiation inlet and along the interior of the waveguide, to be absorbed by each of the plural specific gases therein; and means for analyzing the laser radiation emerging from the outlet, after said absorption; and for, based on said analyzing, then deriving and recording spectra for the plural specific gases of the gaseous specimen.

50. An apparatus for detecting and determining a concentration of plural respective specific gases within a gaseous mixture specimen; said apparatus comprising:

a tunable laser selectively providing radiation of plural wavelengths for use in monitoring plural gases;

a coiled hollow waveguide adapted for guiding radiation along an interior of the waveguide and having:

an inlet for radiation from the tunable laser, said inlet having substantially no conical radiation coupler, and a waveguide interior with inside diameter of two millimeters or less, and radius of curvature equal to approximately five centimeters, or more, at substantially all points along the waveguide, and an outlet for radiation from the tunable laser after passage along the waveguide, said outlet having no conical radiation coupler;

means for providing multiple substantially parallel and discrete paths for directed flow of the gaseous specimen longitudinally within the waveguide interior;

means for projecting the laser radiation into the radiation inlet and along the interior of the waveguide, to be absorbed by each of the plural specific gases therein; and means for analyzing the laser radiation emerging from the outlet, after said absorption; and for, based on said analyzing, then deriving and recording spectra for the plural specific gases of the gaseous specimen;

wherein the providing means comprise sets of perforations formed in distinct groupings in respective gas intake and gas exhaust regions along the waveguide.

51. The apparatus of claim 50, wherein:

the perforations comprise one pair of perforation sets for substantially each coil of the coiled waveguide; and the perforation sets of each pair are respectively disposed in different sectors of the coil corresponding to that pair.

52. The apparatus of claim 50, wherein:

the perforations comprise one pair of perforation sets for substantially each coil of the coiled waveguide; and the perforation sets of each pair are respectively disposed in substantially opposed sectors of the coil corresponding to that pair.

53. A handheld self-contained portable apparatus for detecting and measuring at least one gas within a gaseous specimen by radiation-absorption spectroscopy, the apparatus being for use with a portable source of energy for powering the apparatus; said apparatus comprising:

a coiled waveguide having a radiation inlet and a radiation outlet, and having an interior, and being adapted for guiding radiation along the interior;

means for providing flow of the specimen within the interior of the waveguide;

means for projecting radiation along the interior of the waveguide to irradiate the gaseous specimen;

means for analyzing the radiation emerging from the gaseous specimen to detect and determine the concentration of at least one gas in the specimen; and housing means for enclosing the waveguide, the projecting means, the analyzing means, the path-providing means and the flow-providing means; and having overall dimensions of approximately twenty-five centimeters by thirty centimeters by eight centimeters, or less;

wherein the housing means comprise a housing supporting the waveguide in coiled loops, the housing having:

an intake chamber enclosing a first portion of the loops and receiving the gaseous specimen therein, and an exhaust chamber enclosing a second portion of the loops and exhausting the gaseous specimen therefrom, and a bulkhead through which the loops sealingly pass and which separates the intake chamber from the exhaust chamber; and means for controlling the apparatus; and means for displaying the analysis of the apparatus;

said apparatus weighing approximately three kilograms, or less.

54. A method for adapting an elongated hollow waveguide, having a wall and an interior, for flow of a gaseous specimen through the wall; said method comprising the steps of:

providing an elongated hollow waveguide that is flexible;

forming at least one perforated opening through a first portion of the wall for intake of the gaseous specimen; and forming at least one perforated opening through a second portion of the wall, distinctly separated longitudinally along the waveguide from the first portion, for exhaust of the gaseous specimen; and establishing a dividing structure that sealingly engages the exterior of the waveguide wall, to mutually isolate the intake and exhaust portions except as to flow through the interior of the waveguide.

55. The method of claim 54:

further comprising the step of curving the flexible waveguide into arcuate shapes each having a convex side and a concave side; and wherein the opening-forming steps comprise perforating portions of the wall at exclusively the concave side of substantially each arcuate shape.

56. A method for adapting an elongated hollow waveguide having a wall and an interior, for a plurality of paths of flow of a gaseous specimen through the wall; said method comprising the steps of:

securing the waveguide into a coil having multiple loops, with a gas intake portion of substantially each loop and a gas exhaust portion of substantially each loop at opposed sides of the coil;

forming at least one perforated opening through the wall of substantially each loop in the intake portion for intake of the gaseous specimen;

forming at least one perforated opening through the wall of substantially each loop in the exhaust portion for exhaust of the gaseous specimen;

whereby substantially each perforated loop provides two roughly half-loop paths for the gaseous mixture to flow from the entry portion to the exhaust portion; and establishing a dividing structure, generally diametrally across the coil, to mutually isolate the intake and exhaust portions except as to flow through the interior of the waveguide.

57. The method of claim 56, wherein:

the opening-forming steps comprise perforating portions of the wall at exclusively the inside diameter of the coil.

* * * * *